(12) United States Patent
Benson et al.

(10) Patent No.: US 11,589,905 B2
(45) Date of Patent: *Feb. 28, 2023

(54) SET SCREW SENSOR PLACEMENT

(71) Applicant: Warsaw Orthopedic, Inc., Warsaw, IN (US)

(72) Inventors: Nicholas Benson, Collierville, TN (US); Newton H Metcalf, Jr., Memphis, TN (US); Arjun S. Kurian, Memphis, TN (US); John Coleman, Collierville, TN (US); Charles Murrell, Olive Branch, MS (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 776 days.

This patent is subject to a terminal disclaimer.

(21) Appl. No.: 16/395,216

(22) Filed: Apr. 25, 2019

(65) Prior Publication Data
US 2020/0022740 A1 Jan. 23, 2020

Related U.S. Application Data

(63) Continuation-in-part of application No. 16/039,592, filed on Jul. 19, 2018, now Pat. No. 11,298,162.

(51) Int. Cl.
*A61B 17/70* (2006.01)
*A61F 2/46* (2006.01)
(Continued)

(52) U.S. Cl.
CPC .......... *A61B 17/7091* (2013.01); *A61B 5/076* (2013.01); *A61B 17/7076* (2013.01);
(Continued)

(58) Field of Classification Search
CPC ......... A61F 2002/4666; A61B 17/7074; A61B 17/7032; A61B 17/7034;
(Continued)

(56) References Cited

U.S. PATENT DOCUMENTS 5,697,929 A 12/1997 Mellinger
6,004,349 A 12/1999 Jackson
(Continued)

FOREIGN PATENT DOCUMENTS

JP 2015532841 A 11/2015
KR 10-1851690 B1 4/2018
(Continued)

OTHER PUBLICATIONS

International Search Report, PCT/US2019/042511, dated Oct. 31, 2019.
(Continued)

*Primary Examiner* — Devin B Henson
*Assistant Examiner* — H. Q. Nguyen
(74) *Attorney, Agent, or Firm* — Fox Rothschild LLP

(57) ABSTRACT

A load sensing assembly for a spinal implant includes a set screw having a central opening that extends from a first end of the set screw toward a second end of the set screw. The second end of the set screw is configured to engage with an anchoring member. The load sensing assembly includes an antenna, an integrated circuit in communication with the antenna, where the integrated circuit is positioned within the central opening of the set screw, and a strain gauge in connection with the integrated circuit. The strain gauge is located within the central opening of the set screw in proximity to the second end of the set screw.

19 Claims, 16 Drawing Sheets

(51) Int. Cl.
*A61B 5/07* (2006.01)
*G01L 5/00* (2006.01)
*A61B 90/00* (2016.01)

(52) U.S. Cl.
CPC .......... *A61F 2/4657* (2013.01); *G01L 5/0004* (2013.01); *A61B 17/7035* (2013.01); *A61B 2090/064* (2016.02); *A61B 2562/0261* (2013.01); *A61F 2002/4666* (2013.01)

(58) Field of Classification Search
CPC .......... A61B 2562/0261; A61B 5/4566; A61B 5/4851; A61B 5/6878; A61B 5/0031; A61B 5/076; A61B 2090/064–065; A61B 2017/0425; A61B 2017/044; A61B 2017/0453; A61B 17/686; A61B 17/7082; A61B 17/7083; A61B 17/7085; A61B 17/7086; A61B 17/7088; A61B 17/7089; A61B 17/7091; A61B 17/7092; A61B 17/7001; A61B 17/7002; A61B 17/7004; A61B 17/7005; A61B 17/7007; A61B 17/7008; A61B 17/701; A61B 17/7011; A61B 17/7013; A61B 17/7014; A61B 17/7019; A61B 17/702; A61B 17/7035; A61B 17/7037; A61B 17/7038; A61B 17/704; A61B 17/7041; A61B 17/7043; A61B 17/7044; A61B 17/7046; A61B 17/7058; F16B 35/005
See application file for complete search history.

(56) References Cited

U.S. PATENT DOCUMENTS

| | | | |
|---|---|---|---|
| 6,179,841 B1 | 1/2001 | Jackson | |
| 6,280,445 B1 | 8/2001 | Morrison et al. | |
| 6,485,491 B1 | 11/2002 | Farris et al. | |
| 6,884,244 B1 | 4/2005 | Jackson | |
| 8,057,519 B2 | 11/2011 | Justis et al. | |
| 8,868,200 B2 | 10/2014 | Abrahamson et al. | |
| 9,241,738 B2 | 1/2016 | Quevedo et al. | |
| 9,498,294 B2 | 11/2016 | Rigsby et al. | |
| 9,711,840 B2* | 7/2017 | Lin .................. H01Q 1/12 | |
| 2005/0018749 A1 | 1/2005 | Sato et al. | |
| 2005/0187549 A1 | 8/2005 | Jackson | |
| 2005/0228326 A1 | 10/2005 | Kalfas et al. | |
| 2005/0267477 A1 | 12/2005 | Jackson | |
| 2006/0052782 A1 | 3/2006 | Morgan et al. | |
| 2007/0100218 A1* | 5/2007 | Sweitzer ............ A61B 5/0002 600/323 | |
| 2008/0281212 A1 | 11/2008 | Nunez et al. | |
| 2009/0234391 A1 | 9/2009 | Butler et al. | |
| 2009/0298650 A1 | 12/2009 | Kutliroff | |
| 2010/0152621 A1 | 6/2010 | Janna et al. | |
| 2010/0201118 A1 | 8/2010 | Anton et al. | |
| 2010/0298886 A1 | 11/2010 | Kraus et al. | |
| 2011/0106179 A1 | 5/2011 | Prevost et al. | |
| 2011/0213221 A1 | 9/2011 | Roche | |
| 2011/0319755 A1 | 12/2011 | Stein et al. | |
| 2013/0072982 A1 | 3/2013 | Simonson | |
| 2013/0076157 A1 | 3/2013 | Stein | |
| 2013/0079669 A1 | 3/2013 | Stein et al. | |
| 2013/0079680 A1 | 3/2013 | Stein et al. | |
| 2013/0096396 A1 | 4/2013 | Riedel | |
| 2013/0253334 A1 | 9/2013 | Al-Ali et al. | |
| 2015/0080901 A1 | 3/2015 | Stein | |
| 2016/0331415 A1 | 11/2016 | Serhan et al. | |
| 2017/0007420 A1 | 1/2017 | Stevenson et al. | |
| 2017/0079555 A1 | 3/2017 | Munro et al. | |
| 2017/0138387 A1 | 5/2017 | Saigo et al. | |
| 2017/0196499 A1 | 7/2017 | Hunter | |
| 2017/0196508 A1 | 7/2017 | Hunter | |
| 2017/0231559 A1 | 8/2017 | Cuevas et al. | |
| 2018/0195547 A1 | 7/2018 | Demeocq | |
| 2019/0038214 A1 | 2/2019 | Mikhail et al. | |
| 2020/0022733 A1 | 1/2020 | Benson et al. | |
| 2020/0022735 A1 | 1/2020 | Fields et al. | |
| 2020/0022739 A1 | 1/2020 | Benson et al. | |
| 2020/0022740 A1 | 1/2020 | Benson et al. | |
| 2020/0022772 A1 | 1/2020 | Benson et al. | |
| 2020/0085366 A1 | 3/2020 | Benson et al. | |

FOREIGN PATENT DOCUMENTS

| | | |
|---|---|---|
| WO | 2013109762 A1 | 7/2013 |
| WO | 2015200720 A2 | 12/2015 |
| WO | 2017006068 A1 | 1/2017 |
| WO | 2017007821 A1 | 1/2017 |
| WO | 2017165717 A1 | 9/2017 |
| WO | 2017180653 A1 | 10/2017 |

OTHER PUBLICATIONS

International Search Report, PCT/US2019/042516, dated Oct. 31, 2019.
International Search Report and Written Opinion, PCT/US2020/041487 dated Nov. 2, 2020.
European Search Report in Application No. 21168012.9 dated Sep. 20, 2021.
International Search Report and Written Opinion in Application No. PCTUS2019050717 dated Jan. 3, 2020.
Rodriguez-Martin, et al. "A wearable inertial measurement unit for long-term monitoring in the dependency care area." Sensors 13.10 (2013): 14079-14104. (Year: 2016).
Conway, Justin, Christy C. Tomkins, and Andrew J. Haig. "Walking assessment in people with lumbar spinal stenosis: capacity, performance, and self-report measures." The Spine Journal 11.9 (2011): 816-823. (Year: 2011).
Trost, et al. "Conducting accelerometer-based activity assessments in field-based research." Medicine & Science in Sports & Exercise 37.11 (2005): S531-S543. (Year: 2005).
Liu, Ye, et al. "From action to activity: sensor-based activity recognition." Neurocomputing 181 (2016): 108-115. (Year: 2016).
Ahmadi, Amin, et al. "Automatic activity classification and movement assessment during a sports training session using wearable inertial sensors." 2014 11th International Conference on Wearable and Implantable Body Sensor Networks. IEEE, 2014. (Year: 2014).
European Search Report in Application No. 19838911.6 dated Apr. 4, 2022.
European Search Report in Application No. 19838132.9 dated Apr. 4, 2022.
European Search Report in Application No. 19837036.3 dated Apr. 4, 2022.

* cited by examiner

SET SCREW SENSOR PLACEMENT

CROSS-REFERENCE TO RELATED U.S. PATENT APPLICATION

This application claims benefit to U.S. Nonprovisional patent application Ser. No. 16/039,592, entitled "LOAD SENSING ASSEMBLY FOR A SPINAL IMPLANT", filed Jul. 19, 2018, which is incorporated herein by reference in its entirety.

TECHNICAL FIELD

The present disclosure generally relates to load sensing assemblies for implant devices, and more particularly to load sensing assemblies for implant devices that are used to treat various spinal disorders.

BACKGROUND

Treatment of spinal disorders, such as degenerative disc disease, disc herniations, scoliosis or other curvature abnormalities, and fractures, often requires surgical treatments. For example, spinal fusion may be used to limit motion between vertebral members. As another example, implants may be used to preserve motion between vertebral members.

Surgical treatment typically involves the use of longitudinal members, such as spinal rods. Longitudinal members may be attached to the exterior of two or more vertebral members to assist with the treatment of a spinal disorder. Longitudinal members may provide a stable, rigid column that helps bones to fuse, and may redirect stresses over a wider area away from a damaged or defective region. Also, rigid longitudinal members may help in spinal alignment.

Screw assemblies may be used to connect a longitudinal member to a vertebral member. A screw assembly may include a pedicle screw, hook, or other connector and/or a set screw, among other components. A pedicle screw can be placed in, above and/or below vertebral members that were fused, and a longitudinal member can be used to connect the pedicle screws which inhibits or controls movement. A set screw can be used to secure the connection of a longitudinal member and a pedicle screw, hook or other connector. However, the connection force and continued integrity of the connection between a longitudinal member and a pedicle screw or other connector can be challenging to monitor during and after implantation. In addition, it is difficult to monitor that a proper or acceptable or any force is maintained between a set screw and a longitudinal member.

SUMMARY

In an embodiment, a load sensing assembly for a spinal implant includes a set screw having a central opening that extends from a first end of the set screw toward a second end of the set screw. The second end of the set screw is configured to engage with an anchoring member. The load sensing assembly includes an antenna, an integrated circuit in communication with the antenna, where the integrated circuit is positioned within the central opening of the set screw, and a strain gauge in connection with the integrated circuit. The strain gauge is located within the central opening of the set screw in proximity to the second end of the set screw.

In an embodiment, the antenna may include an opening there through, where the antenna circumferentially surrounds at least a portion of the set screw. Alternatively, at least a portion of the antenna may be positioned in the central opening of the set screw.

The load sensing assembly may include an electronics component having a top surface, a bottom surface, and one or more electrical circuits. The integrated circuit may be positioned on the top surface of the electronics component. The strain gauge may be operably connected to the bottom surface of the electronics component.

In an embodiment, the strain gauge may be configured to measure a force between the set screw and a longitudinal member when the set screw is engaged with the anchoring member.

The integrated circuit may include memory, and the integrated circuit may be configured to store one or more measurements made by the strain gauge in the memory, and transmit the one or more measurements to a reader when the reader is in proximity to the integrated circuit.

In an embodiment, the integrated circuit may include memory, and the integrated circuit may be configured to store a unique identifier associated with the set screw in the memory, and transmit the unique identifier to a reader when the reader is in proximity to the integrated circuit.

In an embodiment, the load sensing assembly may include an anchoring member having a channel that is configured to receive a longitudinal member and a second strain gauge located within the channel. The second strain gauge may be configured to measure a force between the anchoring member and the longitudinal member when positioned in the channel.

In various embodiments, the integrated circuit may include one or more of the following radio frequency identification (RFID) chip, or a near-field communication (NFC) chip.

In an embodiment, a load sensing assembly for a spinal implant includes an anchoring member having a head and a base. The head includes a channel that is configured to receive a longitudinal member, and one or more head openings that extend from an external portion of the head into the channel. The load sensing assembly includes an antenna having an opening there through, wherein the antenna circumferentially surrounds at least a portion of the base of the anchoring member, and an integrated circuit in communication with the antenna, where the integrated circuit is positioned within the channel via at least one of the head openings. The load sensing assembly includes a strain gauge located within the channel, where the strain gauge is configured to measure a force between the anchoring member and the longitudinal member when positioned in the channel.

Optionally, the load sensing assembly may include an electronics component having one or more electrical circuits. The integrated circuit may be connected to the electronics component. The strain gauge may be operably connected to the electronics component via a connecting member.

In an embodiment, the integrated circuit may include memory, and the integrated circuit may be configured to store one or more measurements made by the strain gauge in the memory, and transmit the one or more measurements to a reader when the reader is in proximity to the integrated circuit.

In an embodiment, the integrated circuit may include memory, and the integrated circuit may be configured to store a unique identifier associated with the anchoring member in the memory, and transmit the unique identifier to a reader when the reader is in proximity to the integrated circuit.

A load sensing assembly may further include a set screw having a central opening that extends from a first end of the set screw toward a second end of the set screw, where the second end of the set screw may be configured to engage with the anchoring member, and a second strain gauge located within the central opening of the set screw in proximity to the second end of the set screw.

In an embodiment, the integrated circuit may include one or more of the following radio frequency identification (RFID) chip, or a near-field communication (NFC) chip.

In an embodiment, a load sensing assembly for a spinal implant includes an antenna, an electronics component having one or more electrical circuits that is operably connected to the antenna, an integrated circuit operably connected to at least a portion of the electronics component, and a strain gauge in communication with the integrated circuit, where the strain gauge is configured to measure a force between the implant and a longitudinal member.

The electronics component may be operably connected to the antenna via a connecting member that extends perpendicularly to the antenna. The antenna may include a radio frequency identification coil, and the antenna may be configured to circumferentially surround at least a portion of a set screw or a pedicle screw.

In an embodiment, at least a portion of the antenna may be positioned in a central opening of a set screw.

In an embodiment, the integrated circuit may include memory, and the integrated circuit may be configured to store one or more measurements made by the strain gauge in the memory, and transmit the one or more measurements to a reader when the reader is in proximity to the integrated circuit.

The integrated circuit may include memory, and the integrated circuit may be configured to store a unique identifier associated with the implant in the memory, and transmit the unique identifier to a reader when the reader is in proximity to the integrated circuit.

In an embodiment, a load sensing assembly for a spinal implant may include a set screw including a central opening that extends from a first end of the set screw toward a second end of the set screw. In one or more cases, the second end of the set screw is configured to engage with an anchoring member. In one or more cases, the load sensing assembly may include an antenna. In one or more cases, the load sensing assembly may include an integrated circuit in communication with the antenna. In one or more cases, the integrated circuit is positioned within the central opening of the set screw. In one or more cases, the load sensing assembly may include a plurality of sensors in connection with the integrated circuit. In one or more cases, the plurality of sensors may be located within the central opening of the set screw in proximity to the second end of the set screw.

In an embodiment, a load sensing assembly for a spinal implant may include an antenna. In one or more cases, the load sensing assembly may include an electronics component including one or more electrical circuits. In one or more cases, the electronics component may be operably connected to the antenna. In one or more cases, the load sensing assembly may include an integrated circuit operably connected to at least a portion of the electronics component. In one or more cases, the load sensing assembly may include a plurality of sensors in communication with the integrated circuit. In one or more cases, the plurality of sensors may be configured to measure a force between the implant and a longitudinal member. In one or more cases, the plurality of sensors may be arranged on and operably connected to the bottom surface of the electronics component.

DETAILED DESCRIPTION

Figure 1:
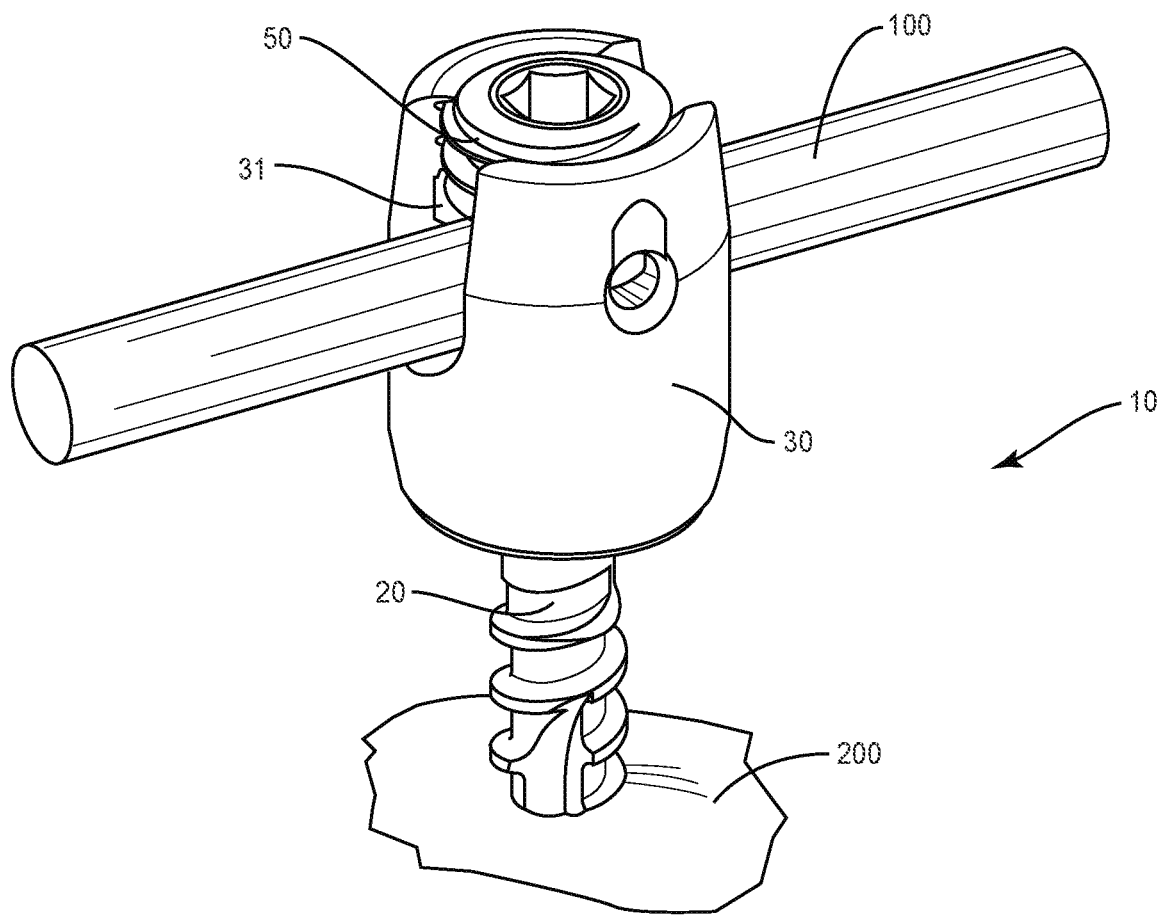
FIG. 1 illustrates an example anchoring assembly and longitudinal member according to an embodiment.

The exemplary embodiments of the surgical system and related methods of use disclosed are discussed in terms of medical devices for the treatment of musculoskeletal disorders and more particularly, in terms of a vertebral fixation screws, including for example pedicle screws, as well as hooks, cross connectors, offset connectors and related systems for use during various spinal procedures or other orthopedic procedures and that may be used in conjunction with other devices and instruments related to spinal treatment, such as rods, wires, plates, intervertebral implants, and other spinal or orthopedic implants, insertion instruments, specialized instruments such as, for example, delivery devices (including various types of cannula) for the delivery of these various spinal or other implants to the vertebra or other areas within a patient in various directions, and/or a method or methods for treating a spine, such as open procedures, mini-open procedures, or minimally invasive procedures. Exemplary prior art devices that may be modified to include the various embodiments of load sensing systems include, for example, U.S. Pat. Nos. 6,485,491 and 8,057,519, all incorporated herein by reference in their entirety.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting.

In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Generally, similar spatial references of different aspects or components indicate similar spatial orientation and/or positioning, i.e., that each "first end" is situated on or directed towards the same end of the device. Further, the use of various spatial terminology herein should not be interpreted to limit the various insertion techniques or orientations of the implant relative to the positions in the spine.

The following discussion includes a description of a vertebral pedicle screw system and related components and methods of employing the vertebral pedicle screw in accordance with the principles of the present disclosure. Reference is made in detail to the exemplary embodiments of the present disclosure, which are illustrated in the accompanying figures.

The components of the vertebral pedicle screw system described herein can be fabricated from biologically acceptable materials suitable for medical applications, including metals, synthetic polymers, ceramics and bone material and/or their composites. For example, the components of the vertebral pedicle screw system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the vertebral pedicle screw system may be formed or constructed material composites, including the above materials, to achieve various desired characteristics such as strength, rigidity, elasticity, compliance, biomechanical performance, durability and radiolucency or imaging preference. The components of the present vertebral pedicle screw system, individually or collectively, may also be fabricated from a heterogeneous material such as a combination of two or more of the above-described materials. The components of the vertebral pedicle screw system may be monolithically formed, integrally connected or include fastening elements and/or instruments, as described herein. The components of the vertebral pedicle screw system may be formed using a variety of subtractive and additive manufacturing techniques, including, but not limited to machining, milling, extruding, molding, 3D-printing, sintering, coating, vapor deposition, and laser/beam melting. Furthermore, various components of the vertebral pedicle screw system may be coated or treated with a variety of additives or coatings to improve biocompatibility, bone growth promotion or other features. To the extent the plate is entirely or partially radiolucent, it may further include radiographic markers made, for example of metallic pins, at one or both ends, on each corner of the ends, and/or along the length of the implant in various locations including near the center of the assembly.

The vertebral pedicle screw system may be employed, for example, with a minimally invasive procedure, including percutaneous techniques, mini-open and open surgical techniques to deliver and introduce instrumentation and/or one or more spinal implants at a surgical site within a body of a patient, for example, a section of a spine. In some embodiments, the vertebral pedicle screw system may be employed with surgical procedures, as described herein, and/or, for example, corpectomy, discectomy, fusion and/or fixation treatments that employ spinal implants to restore the mechanical support function of vertebrae. In some embodiments, the pedicle screw system may be employed with surgical approaches, including but not limited to: anterior lumbar interbody fusion (ALIF), direct lateral interbody fusion (DLIF), oblique lateral lumbar interbody fusion (OLLIF), oblique lateral interbody fusion (OLIF), various types of anterior fusion procedures, and any fusion procedure in any portion of the spinal column (sacral, lumbar, thoracic, and cervical, for example).

FIG. 1 illustrates an example anchoring assembly and longitudinal member according to an embodiment. As illustrated in FIG. 1, an anchoring assembly includes a screw 20 and an anchoring member 30. The screw 20 has an elongated shape with a first end mounted within a vertebral member 200 and a second end extending outward above the vertebral member 200. The anchoring member 30 is configured to operatively connect to the second end of the screw 20 and is movably connected to the screw 20 to accommodate the longitudinal member 100 positioned at various angular positions. The anchoring member 30 includes a channel 31 sized to receive the longitudinal member 100. A set screw 50 attaches to the anchoring member 30 to capture the longitudinal member 100 within the channel 31.

Figure 2:
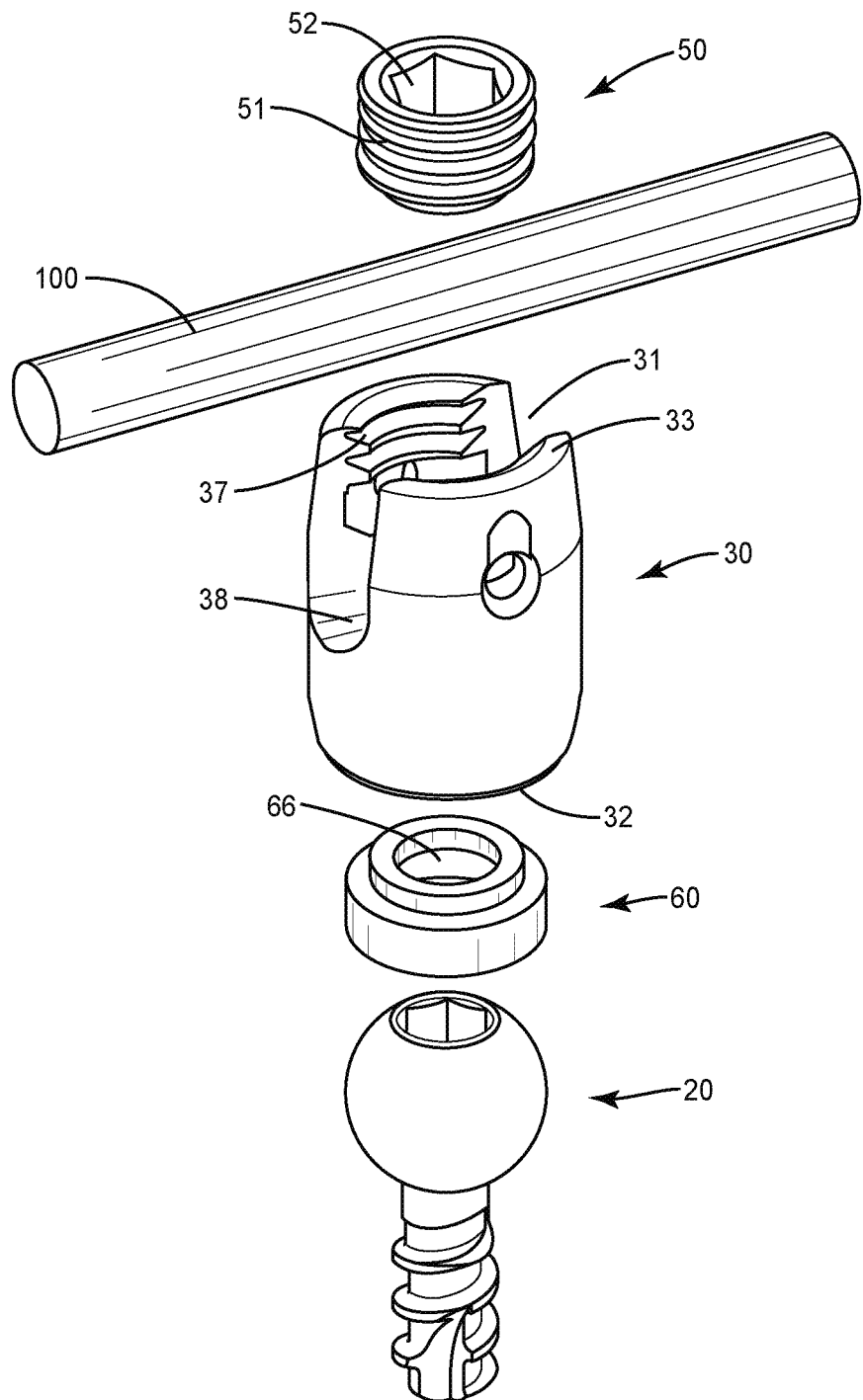
FIG. 2 illustrates an example exploded view of a screw assembly and longitudinal member according to an embodiment.

FIG. 2 illustrates an example exploded view of a screw assembly and longitudinal member according to an embodiment. As shown by FIG. 2, anchoring member 30 provides a connection between the screw 20 and longitudinal member 100. Anchoring member 30 includes a first end 32 that faces towards the vertebral member 200, and a second end 33 that faces away. A chamber is positioned between the first and second ends 32, 33 and is sized to receive at least a portion of the screw 20. In various embodiments, a first end 32 may be considered a base portion of an anchoring member 30, and a second end 33 may be considered a head portion of an anchoring member.

The second end 33 of the anchoring member 30 includes a channel 31 sized to receive the longitudinal member 100. Channel 31 terminates at a lower edge 38 that may include a curved shape to approximate the longitudinal member 100. Threads 37 may be positioned towards the second end 33 to engage with the set screw 50. In one embodiment as illustrated in FIG. 2, the threads 37 are positioned on the interior of the anchoring member 30 facing towards the channel 31. In another embodiment, the threads 37 may be on the exterior of the anchoring member 30. An interior of the anchoring member 30 may be open between the first and second ends 32, 33.

In various embodiments, an anchoring member 30 may include a washer 60. A washer 60 may be generally cylindrical and may have a hole 66 there through. As illustrated by FIG. 1 a washer 60 may be positioned near a first end 32 of an anchoring member 30. A screw 20 may engage with an anchoring member 30 via positioning through the hole 66 of a washer 60. A washer 60 may include recessed portions which may be configured to accommodate placement of a longitudinal member 100 therein. The use of a washer 60 in connection with an anchoring member 30 may help minimize misalignment of the longitudinal member within the anchoring member.

Figure 13A:
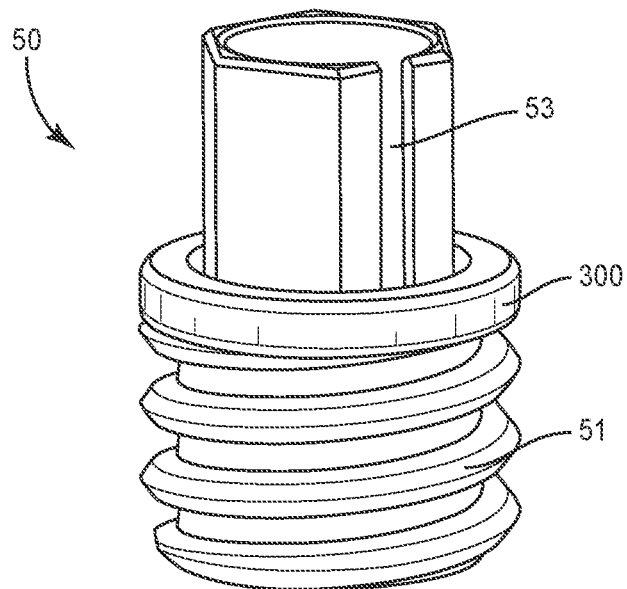
FIGS. 13A and 13B each illustrate an example set screw according to an embodiment.
Figure 13B:
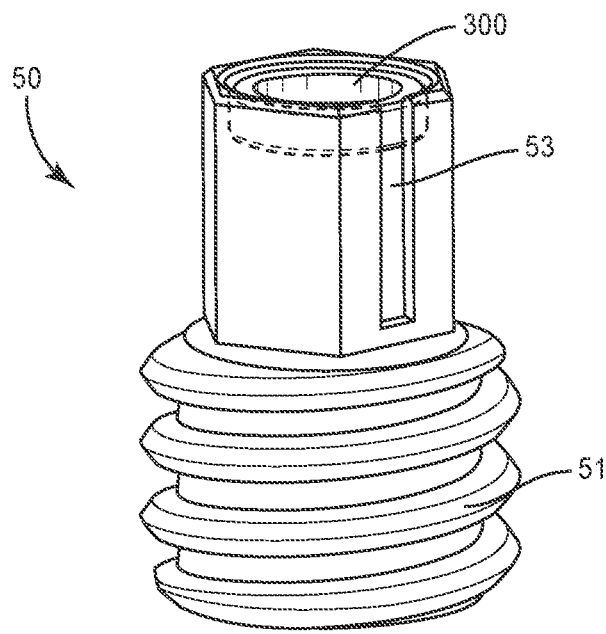

In an embodiment, set screw 50 attaches to the anchoring member 30 and captures the longitudinal member 100 within the channel 31. As illustrated in FIG. 2, the set screw 50 may be sized to fit within the interior of the channel 31 and include exterior threads 51 that engage threads 37 on the anchoring member 30. A driving feature 52 may be positioned on a top side to receive a tool during engagement with the anchoring member 30. In some embodiments, the set screw 50 may be mounted on an exterior of the anchoring member 30. Set screw 50 includes a central opening and is sized to extend around the second end 33. A set screw 50 may be a break-off set screw or a non-break-off set screw. In certain embodiments, a set screw 50 may include a slot 53 for receiving or routing of electronic connections as illustrated in FIGS. 13A and 13B. Threads 51 are positioned on an inner surface of the central opening to engage with the external threads 37 on the anchoring member 30. The set screw 50 and anchoring member 30 may be constructed for the top side of the set screw 50 to be flush with or recessed within the second end 33 when mounted with the anchoring member 30. FIG. 13A illustrates an example set screw 50 having an antenna 300 positioned on an external portion of the set screw. FIG. 13B illustrates an example set screw 50 having an antenna 300 positioned internally in a central opening of the set screw.

Figure 3:
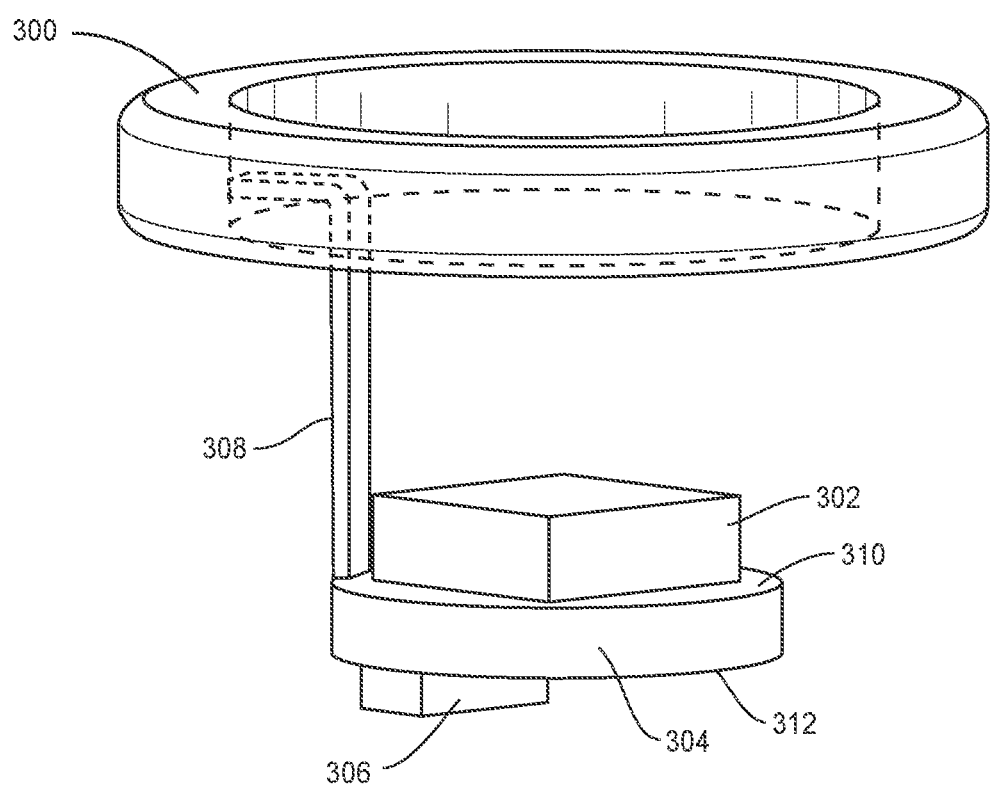
FIG. 3 illustrates an example load sensing assembly for a set screw according to an embodiment.

FIG. 3 illustrates an example load sensing assembly for a set screw according to an embodiment. As illustrated by FIG. 3, a load sensing assembly may include an antenna 300, such as a radio frequency identification (RFID) coil, a near field-communication (NFC) antenna or other short-range communication transmitter and/or receiver. A load sensing assembly may include one or more integrated circuits 302 such as, for example, an RFID chip 302 or an NFC chip. A load sensing assembly may include one or more electronics components 304 and/or a strain gauge 306, such as for example a silicon strain gauge. A strain gauge 306 may be a device that measures strain on an object. For instance, a strain gauge 306 may measure a force between a set screw and a longitudinal member when the set screw is engaged with an anchoring member. A strain gauge 306 may include one or more sensors or sensor nodes that measure strain, force, resistance, load and or the like.

In an embodiment, one or more of the electronics components 304 may include a flexible electronics component, such as, for example, a flex circuit or one or more electrical circuits. The antenna 300 may be operably connected to the electronics component 304 via a connecting member 308. For instance, as shown in FIG. 3, the connecting member 308 may be connected to both the antenna 300 and the electronics component 304. The connecting member 308 may be positioned perpendicularly to both the antenna 300 and the electronics component 304. In various embodiments, a connecting member 308 and an antenna 300 and/or electronics component 304 may be constructed integrally or may be separately constructed and attached together in any suitable manner, such as for example by adhesive, chemical, mechanical or cement bonding.

The integrated circuit 302 may be operably connected to the electronics component 304. For instance, as illustrated in FIG. 3, an electronics component 304 may have a top surface 310 and a bottom surface 312. An integrated circuit 302 may be positioned on the top surface 310 of an electronics component 304, and may be connected to the top surface in any suitable manner, including, for example, adhesive, chemical, mechanical or cement bonding. An integrated circuit 302 may include memory according to an embodiment. The memory may be used to store various information. For example, one or more measurements of a strain gauge 306 may be stored in memory. As another example, a unique identifier associated with a load sensing assembly, a component thereof, or a set screw may be stored in memory. Additional and/or alternate information or types of information may be stored according to this disclosure.

A strain gauge 306 may be operably connected, for example by adhesive, cement, mechanical or chemical bonding, to the electronics component 304. For instance, a strain gauge 306 may be operably connected to the electronics component 304 via the bottom surface 312 of the electronics component 304. A strain gauge 306 may be connected to the bottom surface 312 of an electronics component 304 in any suitable manner including, without limitation, via an adhesive bonding agent.

As shown in FIG. 3, an antenna 300 may have a generally curved shape. The antenna 300 may include a first end and a second end. The antenna 300 may include an opening that extends from the first end toward the second end.

Figure 4A:
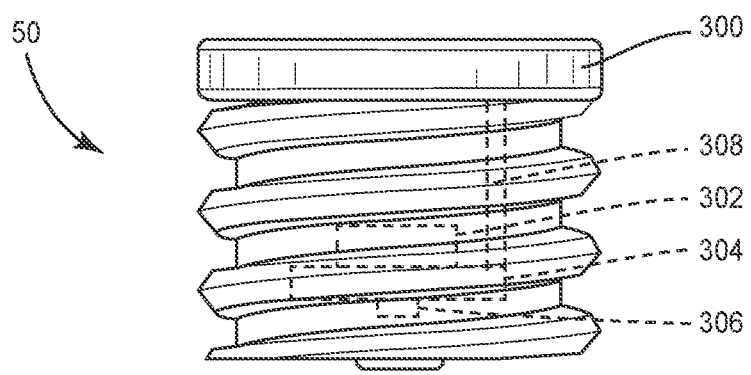
FIGS. 4A and 4B illustrates a load sensing assembly mounted to a set screw according to an embodiment.
Figure 4B:
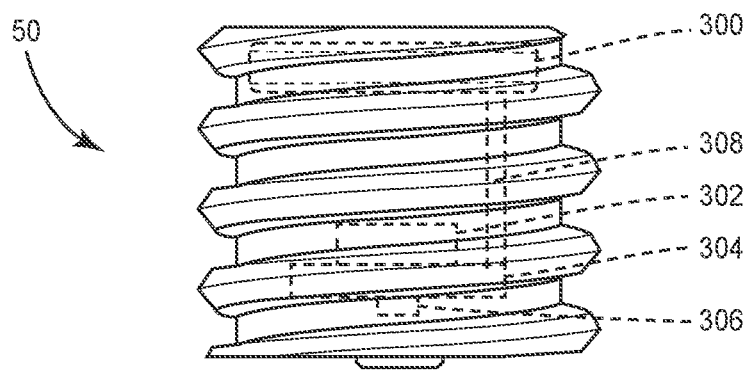

As illustrated in FIG. 4A, a load sensing assembly may be configured to be mounted to a set screw. The antenna 300 is sized to extend around the set screw such that the integrated circuit 302, electronics component 304, strain gauge 306 and connecting member 308 are positioned within the central opening of the set screw as illustrated in FIG. 4A. As illustrated in FIG. 4A, the antenna 300 may circumferentially surround at least a portion of the exterior of the set screw. In other embodiments, as illustrated by FIG. 4B, the antenna 300 may be positioned at least partially inside of the central opening of a set screw.

Figure 5:
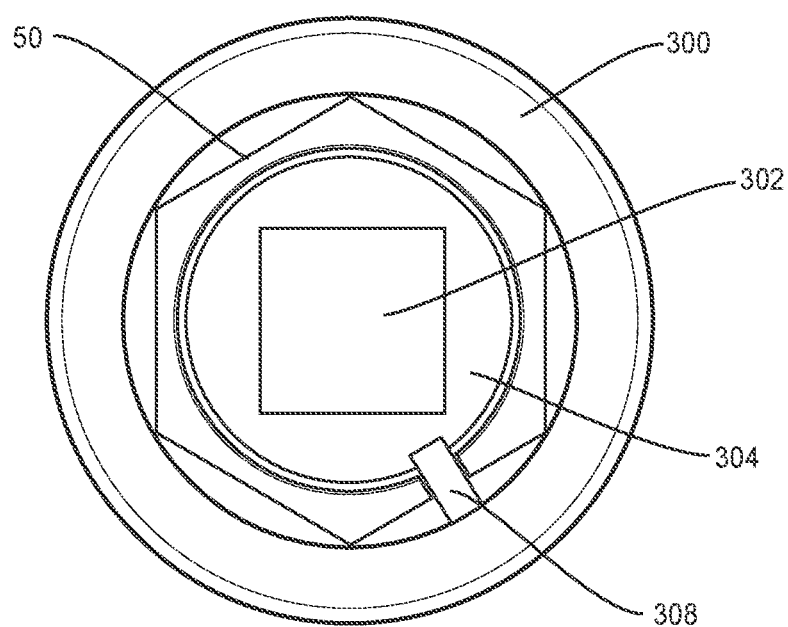
FIG. 5 illustrates a top view of a load sensing assembly mounted to a set screw according to an embodiment.

In certain embodiments, the strain gauge 306 may be connected to a portion of the central opening of the set screw in any suitable manner including, without limitation via an adhesive. The strain gauge 306 may be connected to a portion of the central opening such that it is positioned to measure a force between the set screw and a longitudinal rod when the set screw engages with an anchoring member. FIG. 5 illustrates a top view of a load sensing assembly mounted to a set screw according to an embodiment.

Figure 6:
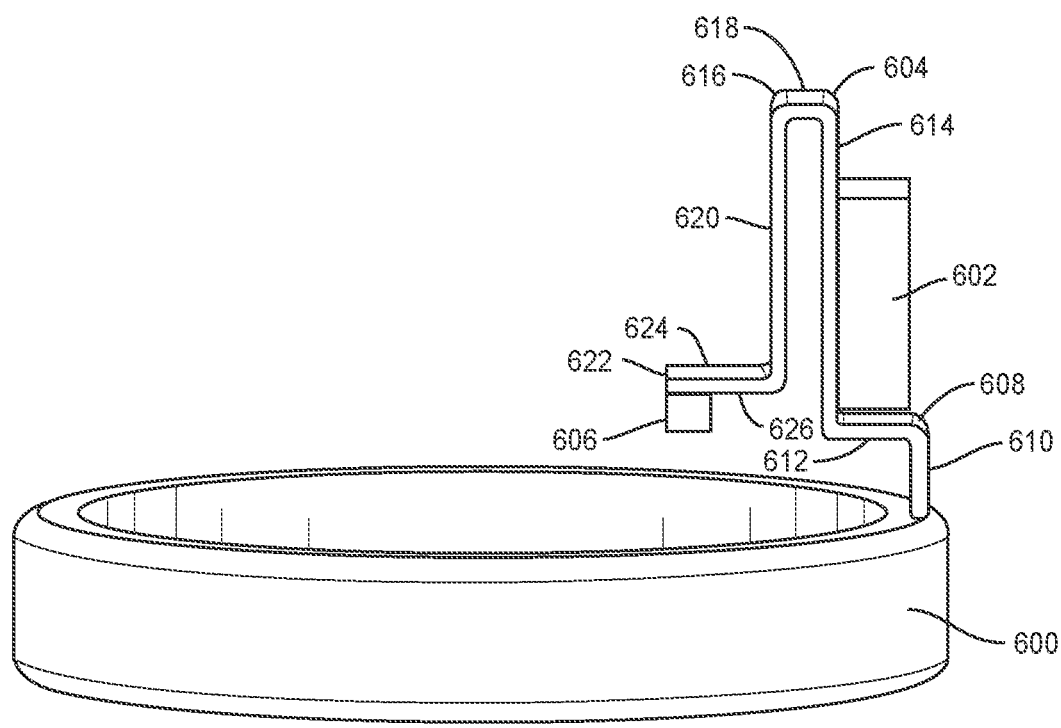
FIG. 6 illustrates an example load sensing assembly according to an embodiment.

FIG. 6 illustrates an example load sensing assembly according to an embodiment. The load sensing assembly illustrated in FIG. 6 may be mounted to an anchoring member according to various embodiments. Example anchoring members may include, without limitation screws, hooks, offset connectors, cross connectors, or other types of anchors or implants. As illustrated in FIG. 6, a load sensing assembly for an anchoring member may include an antenna 600, such as a RFID coil, an NFC antenna or other short-range communication transmitter and/or receiver. A load sensing assembly may include an integrated circuit 602, one or more electronics components 604 and/or a strain gauge 606. In an embodiment, one or more of the electronics components 604 may include a flexible electronics component, such as, for example, a flexible circuit or one or more electrical circuits.

The electronics component 604 may be connected to the antenna 600 via a connecting member 608. As shown in FIG. 6, a connecting member 608 may position an electronics component perpendicularly to the antenna 600. A connecting member 608 may include a first portion 610 that attaches to an antenna 600 and extends substantially vertically and perpendicularly from the antenna. The connecting member 608 may include a second portion 612 connected to the first portion and the electronics component. The second portion 612 may extend substantially horizontally and perpendicularly to the first portion 610. The electronics component 604 may be positioned substantially perpendicularly to the second portion 612. A connecting member 608 may be constructed integrally with an antenna 600 and/or electronics component 604, or may be separately constructed and attached together in any suitable manner.

In various embodiments, the integrated circuit 602 may be connected to a first surface 614 of the electronics component 604 as illustrated in FIG. 6. The RFID chip 602 may be connected to a first surface 614 of an electronics component in any suitable manner. An integrated circuit 602 may include memory according to an embodiment. The memory may be used to store various information. For example, one or more measurements of a strain gauge 606 may be stored in memory. As another example, a unique identifier associated with a load sensing assembly, a component thereof, or an anchoring member may be stored in memory. Additional and/or alternate information or types of information may be stored according to this disclosure.

A strain gauge 606 may be connected to an electronics component 604 via a second connecting member 616. As illustrated in FIG. 6, a second connecting member 616 may include a first portion 618, a second portion 620 and a third portion 622. The first portion 618 may connect to the electronics component 604 and may extend substantially perpendicularly to the electronics component. The second portion 620 of the second connecting member 616 may be connected to the first portion 618 of the second connecting member and may extend substantially perpendicular thereto. The third portion 622 of the second connecting member 616 may be connected to the second portion 620 of the second connecting member, and may extend substantially perpendicular to the second portion.

Figure 7:
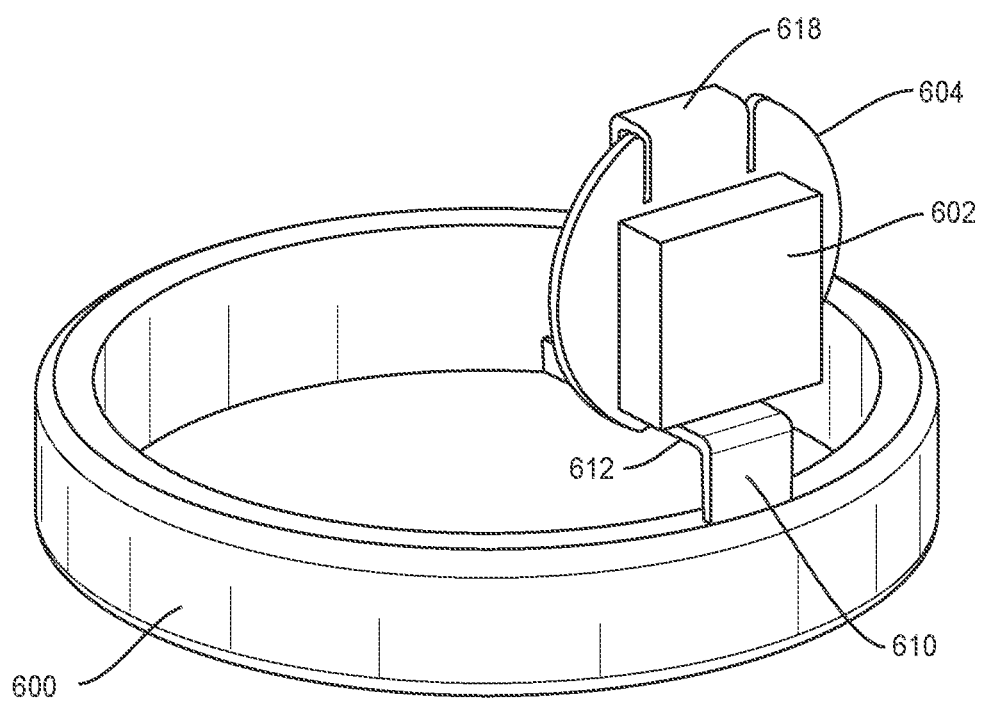
FIG. 7 illustrates a different perspective of a load sensing assembly for an anchoring member according to an embodiment.

The third portion 622 of the second connecting member 616 may have a top surface 624 and a bottom surface 626. A strain gauge 606 may be connected to the bottom surface 626 in any suitable manner. The strain gauge 606 may be configured to measure a force between the set screw and a longitudinal member. FIG. 7 illustrates a different perspective of a load sensing assembly for an anchoring member according to an embodiment.

Figure 8:
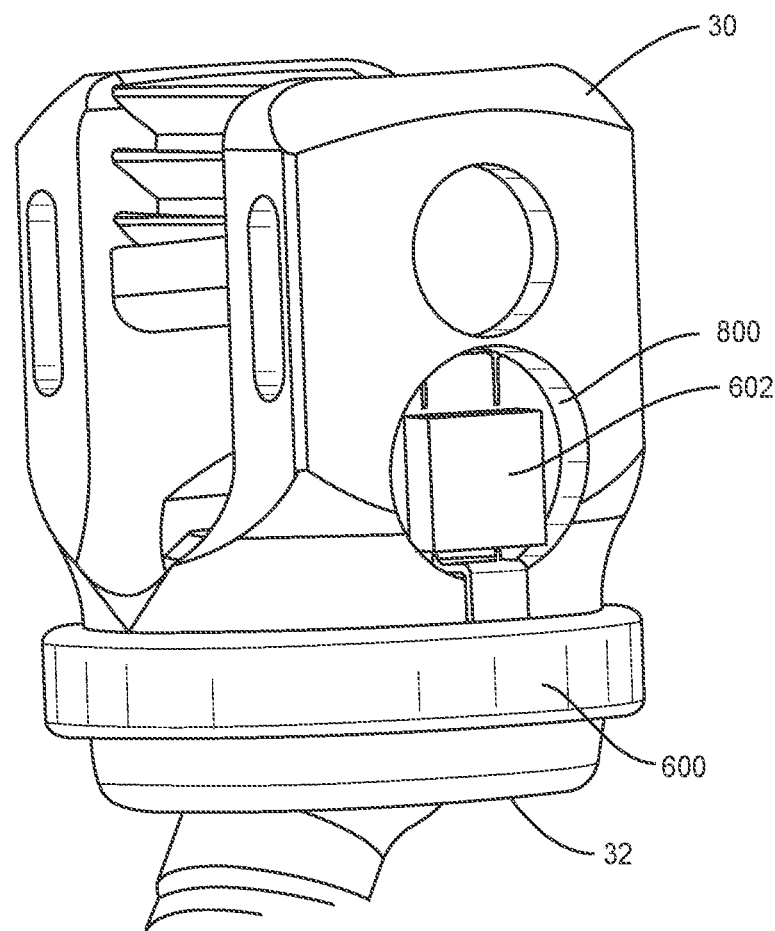
FIG. 8 illustrates a load sensing assembly connected to an anchoring member according to an embodiment.

As illustrated in FIG. 8, a load sensing assembly may be connected to an anchoring member 30. For example, a load sensing assembly may be connected to an anchoring member near a first end 32 of the anchoring member. The antenna 600 is sized to extend around the anchoring member 30, for example, near the first end 32. In various embodiments, an antenna 600 may be securely fitted around a portion of the anchoring member 30. In other embodiments, an antenna 600 may be secured to the anchoring member in any other suitable manner.

Figure 14:
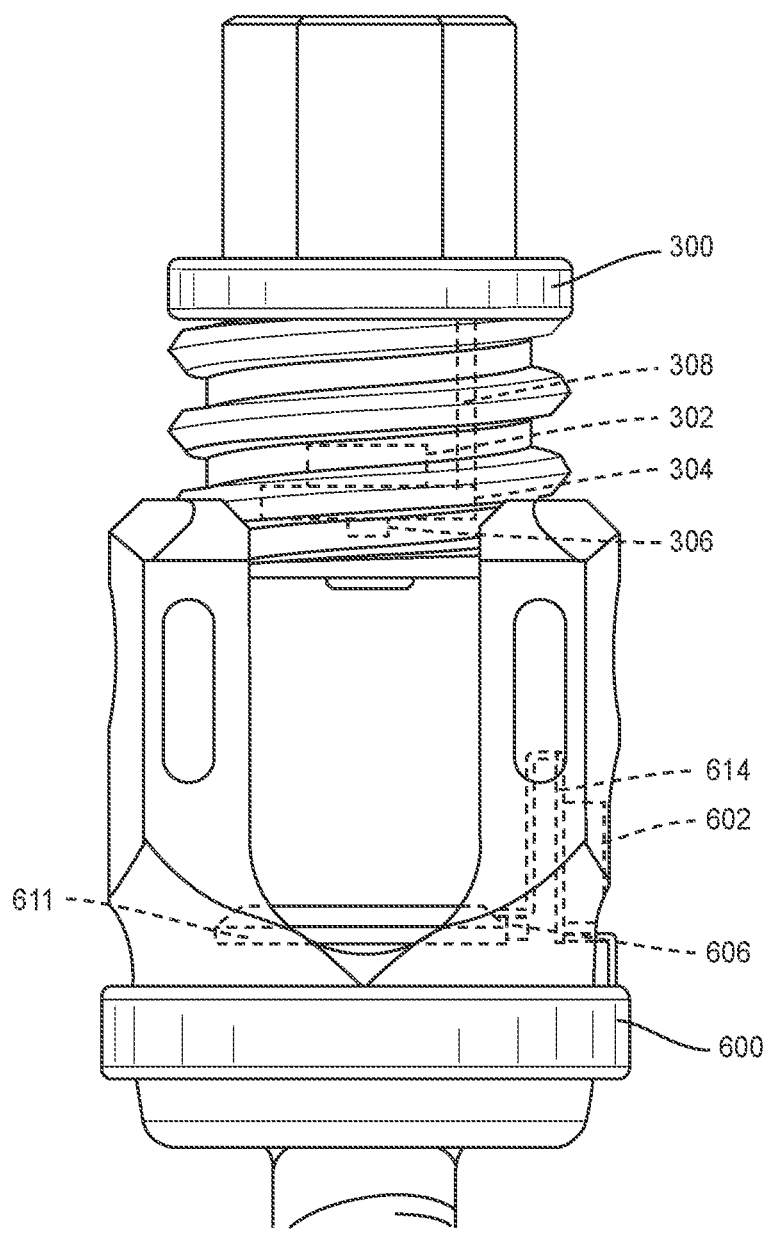
FIG. 14 illustrates an example anchoring member according to an embodiment.

The antenna 600 may be positioned on the anchoring member 30 such that the integrated circuit 602 and electronics component 604 are positioned within an opening of the anchoring member 30. For instance, as illustrated by FIG. 8, an anchoring member 30 may have one or more openings 800 that extend from an outer portion of the anchoring member into the channel 31 of the anchoring member. As illustrated by FIG. 8, the second portion of the first connecting member may extend into the opening 800 and may position the integrated circuit and/or the electronics component within the opening and/or the channel 31. Such a positioning may result in the strain gauge 606 being positioned in the channel 31 at a location where it is possible to measure a force of a longitudinal member in the channel. In an alternate embodiment, a strain gauge 606 may be positioned on or attached to a washer or pressure ring 611 within an anchoring member as illustrated by FIG. 14. In yet another embodiment, in situations where an anchoring member includes a hook member, a strain gauge 606 may be positioned on or attached to a hook portion of the hook member. Measurements obtained by the strain gauge 606 may be used to determine whether a longitudinal member is properly seated and/or torqued during and/or after implant.

Figure 9:
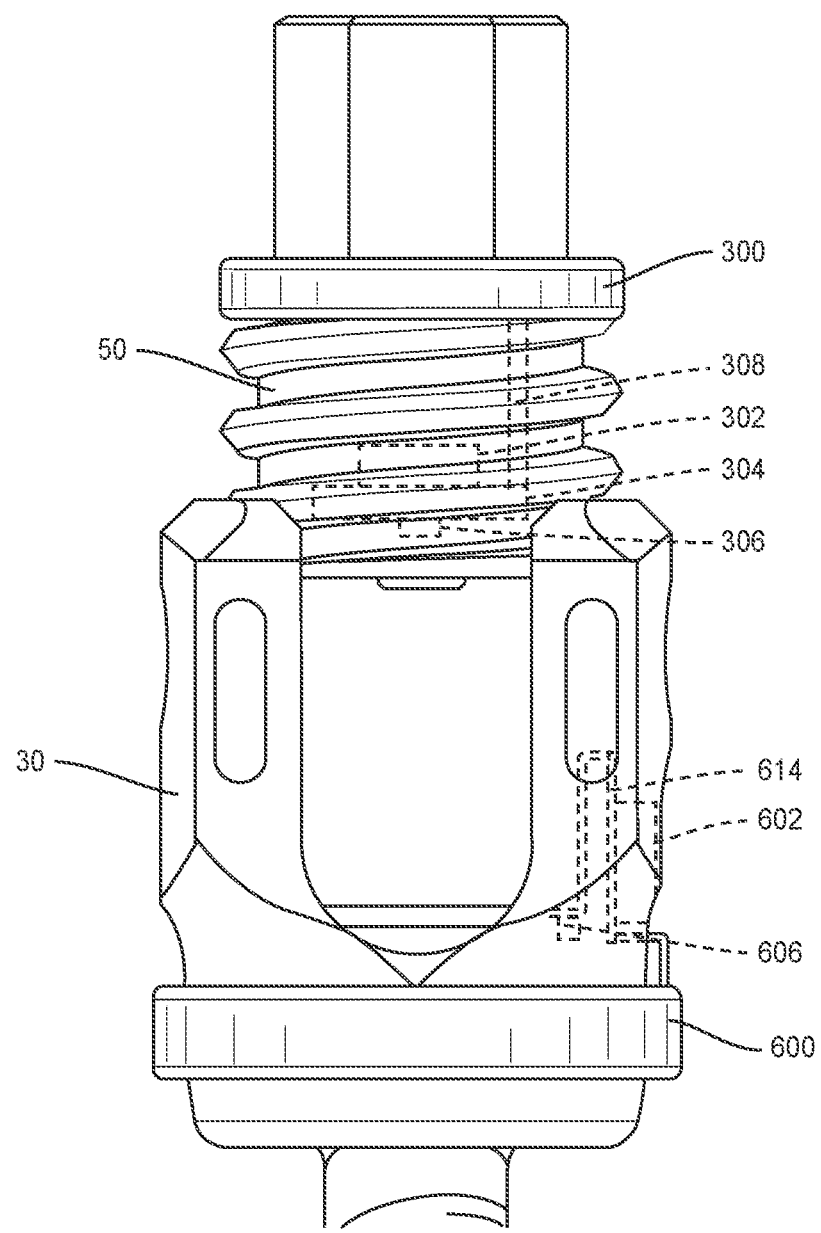
FIG. 9 illustrates a screw assembly set screw having a load sensing assembly and connected to an anchoring member that also has a load sensing assembly mounted to it according to an embodiment.
Figure 10:
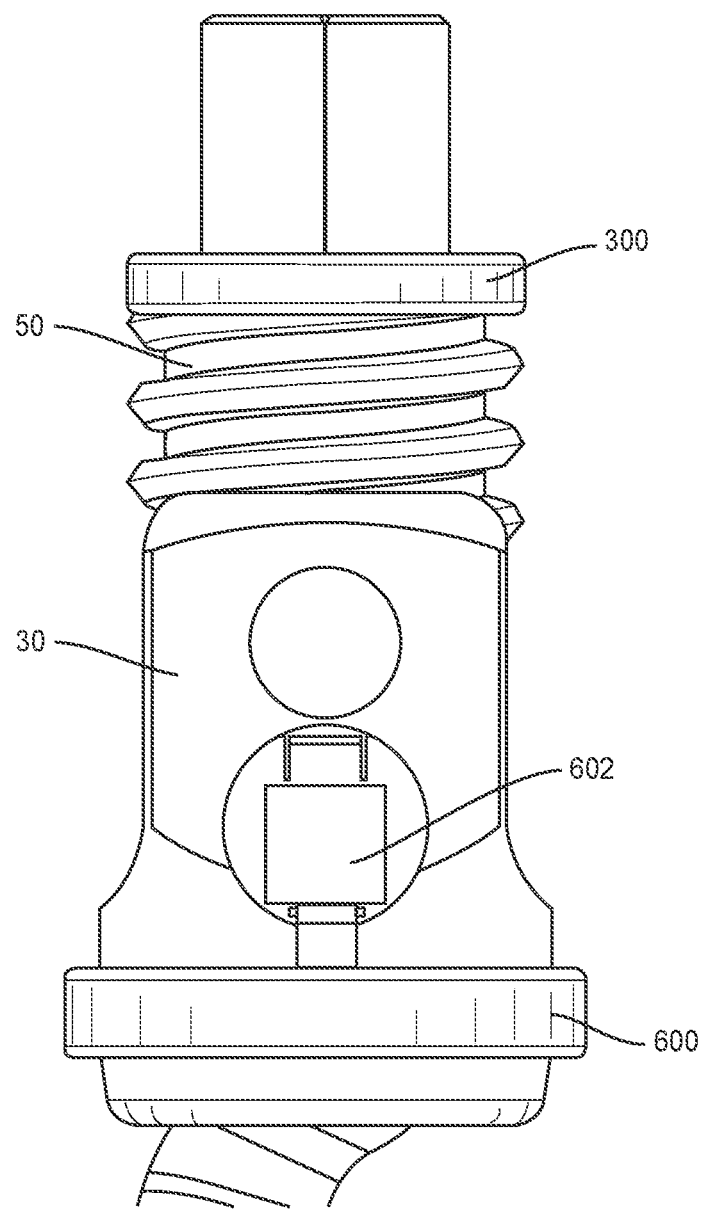
FIG. 10 illustrates a side view of the screw assembly shown in FIG. 9 according to an embodiment.
Figure 11:
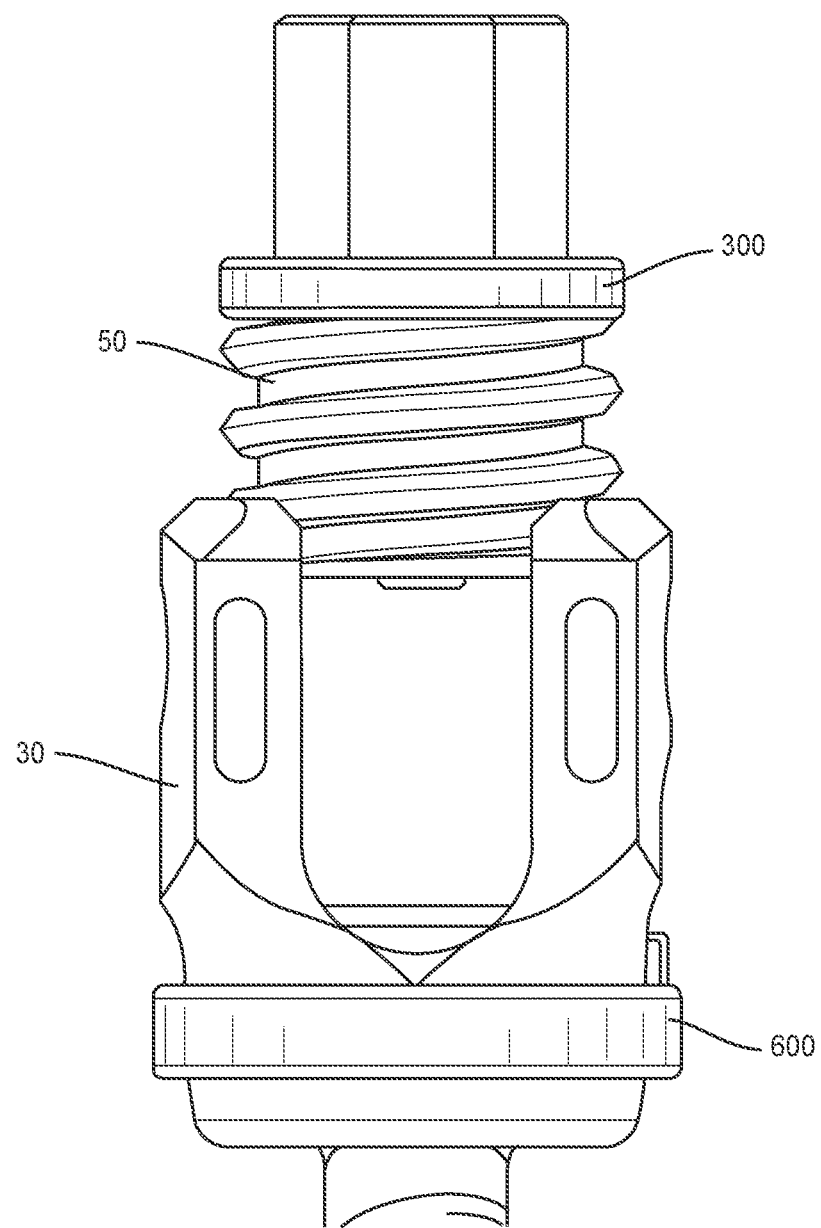
FIG. 11 illustrates a non-transparent view of the screw assembly shown in FIG. 9 according to an embodiment.

In various embodiments, a set screw having a load sensing assembly may be used with in connection with an anchoring member with or without a load, sensing assembly. FIG. 9 illustrates a set screw having a load sensing assembly engaged with an anchoring member that also has a load sensing assembly according to an embodiment. So that components of each can be clearly depicted, a longitudinal member is not shown in FIG. 9. FIG. 10 illustrates a side view of the screw assembly shown in FIG. 9 according to an embodiment. FIG. 11 illustrates a non-transparent view of the screw assembly shown in FIG. 9 according to an embodiment. Although FIGS. 9-11 illustrate an antenna located externally to a set screw, it is understood that the antenna may alternatively be located within at least a portion of the central opening of the set screw.

Figure 12:
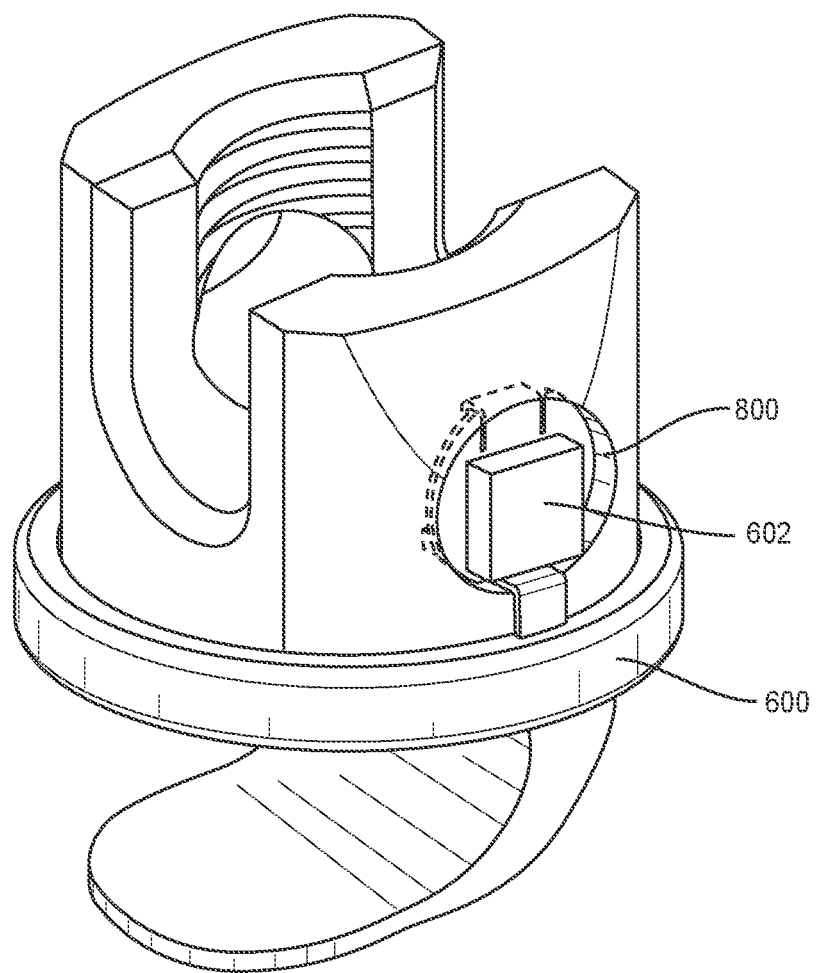
FIG. 12 illustrates an example hook member having a load sensing assembly according to an embodiment.

FIGS. 1-11 illustrate a multi-axial tulip-head pedicle screw according to various embodiments. However, it is understood that other types of anchoring members may be used within the scope of this disclosure. For example, fixed head screws or screws having differently shaped heads may be used. As another example, a hook member, a cross-link connector, an offset connector, or a hybrid hook-screw member may be used as well. FIG. 12 illustrates an example hook member having a load sensing assembly according to an embodiment.

In various embodiments, one or more measurements obtained by a strain gauge may be stored by an integrated circuit of a corresponding load sensing assembly such as, for example, in its memory. The integrated circuit may be interrogated by a reader. For instance, an RFID chip may be read by an RFID reader. As another example, an NFC chip may be read by or may otherwise communicate with an NFC reader or other NFC-enabled device. A reader may interrogate an integrated circuit when in a certain proximity to the integrated circuit. In certain embodiments, a reader may interrogate an integrated circuit that has been implanted into a patient as part of a set screw or anchoring member assembly. In other embodiments, an integrated circuit may communicate with a reader or other electronic device without being interrogated.

An integrated circuit may transmit one or more measurements to the reader. This transmission may occur in response to being interrogated by the reader, or the transmission may be initiated by the integrated circuit. The reader may receive the transmitted measurements, and may cause at least a portion of the measurements to be displayed to a user. For instance, a physician may use a reader to interrogate an RFID chip of a patient's implant. The reader may include a display, or may be in communication with a display device, which may display at least a portion of the measurements received from the RFID chip.

An integrated circuit may be passive, meaning that the chip has no internal power source and is powered by the energy transmitted from a reader. With respect to an assembly having a passive integrated circuit, the integrated circuit may not transmit information until interrogated by a reader.

In another embodiment, an integrated circuit may be active, meaning that the chip is battery-powered and capable of broadcasting its own signal. An active integrated circuit may transmit information in response to be interrogated by a reader, but also on its own without being interrogated. For instance, an active integrated circuit may broadcast a signal that contains certain information such as, for example, one or more measurements gathered by an associated strain gauge. An active integrated circuit may continuously broadcast a signal, or it may periodically broadcast a signal. Power may come from any number of sources, including, for example, thin film batteries with or without encapsulation or piezo electronics.

In various embodiments, one or more sensors of a strain gauge may transmit information by directly modulating a reflected signal, such as an RF signal. The strain gauge sensors may form a Wireless Passive Sensor Network (WPSN), which may utilize modulated backscattering (MB) as a communication technique. External power sources, such as, for example, an RF reader or other reader, may supply a WPSN with energy. The sensor(s) of the WPSN may transmit data by modulating the incident signal from a power source by switching its antenna impedance.

One or more measurements received from a load sensing assembly may be used to make determinations of the condition of a spinal implant and/or treatment of a spinal disorder. For instance, proper placement of a longitudinal member, set screw and/or anchoring member may result in an acceptable range of force measurements collected by a strain gauge of a load sensing assembly. Measurements outside of this range may indicate a problem with the placement or positioning of a longitudinal member, set screw and/or anchoring member such as, for example, loosening of a set screw and/or anchoring member, longitudinal member failure, construct failure, yield or fracture/breakage, improper torque, breakage of the bone segment or portion, the occurrence of fusion or amount of fusion, and/or the like.

One or more tools or instruments may include a reader which may be used to gather information from one or more integrated circuit during or in connection with a procedure. For instance, a torque tool may be used to loosen or tighten a set screw. A torque tool may include a reader, or may be in communication with a reader, such that a user of the torque tool is able to obtain, in substantially real time, one or more measurements relating to the set screw and longitudinal rod placement that are measured by a strain gauge of a load sensing assembly of the set screw via the tool. For instance, as a user is applying torque to a set screw, the user may see one or more force measurements between the set screw and the longitudinal member in order to determine that the positioning of the set screw and/or longitudinal member is correct and that the proper force is being maintained. In certain embodiments, a tool or instrument may include a display device on which one or more measurements may be displayed. In other embodiments, a tool or instrument may be in communication with a display device, and may transmit one or more measurements for display on the display device via a communications network.

In some embodiments, an electronic device, such as a reader or an electronic device in communication with a reader, may compare one or more measurements obtained from an integrated circuit to one or more acceptable value ranges. If one or more of the measurements are outside of an applicable value range, the electronic device may cause a notification to be made. For instance, an electronic device may generate an alert for a user, and cause the alert to be displayed to the user via a display device. Alternatively, an electronic device may send an alert to a user such as via an email message, a text message or otherwise.

An integrated circuit of a load sensing assembly may store a unique identifier associated with the component to which the load sensing assembly corresponds. For instance, an integrated circuit of a load sensing assembly for a set screw may store a unique identifier associated with the set screw. Similarly, an integrated circuit of a load sensing assembly for an anchoring member may store a unique identifier associated with the anchoring member. The integrated circuit may transmit the unique identifier to an electronic device. For instance, when a reader interrogates an integrated circuit, the integrated circuit may transmit a unique identifier for a component that is stored by the integrated circuit to the reader.

Having access to a unique identifier for a component may help a user ascertain whether the measurements that are being obtained are associated with the component of interest. Also, having access to a unique identifier for a component may help a user take inventory of one or more components. For instance, after spinal surgery, a physician or other health care professional may use a reader to confirm that all of the set screws and anchoring members allocated for the procedure have been used and are positioned in a patient.

Figure 15A:
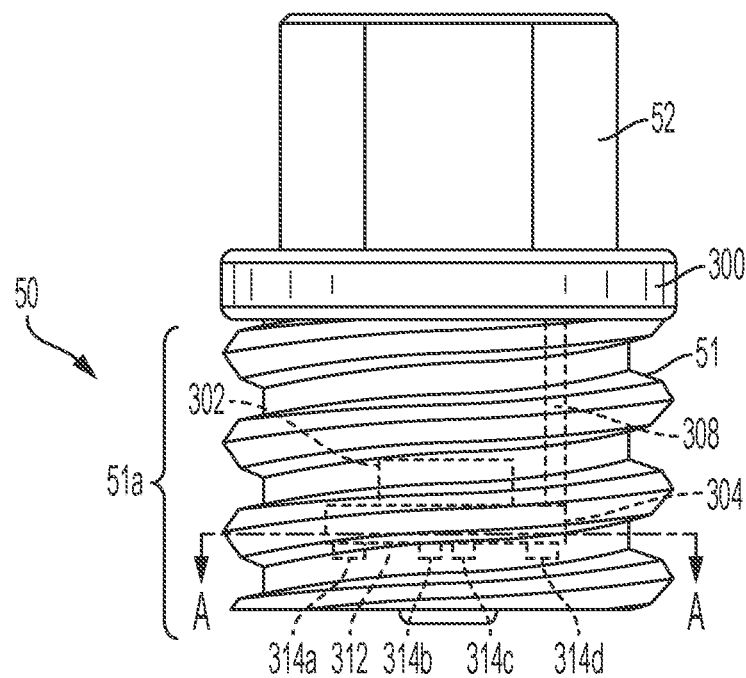
FIG. 15A illustrates a side view of a load sensing assembly mounted to a set screw according to an embodiment.
Figure 15B:
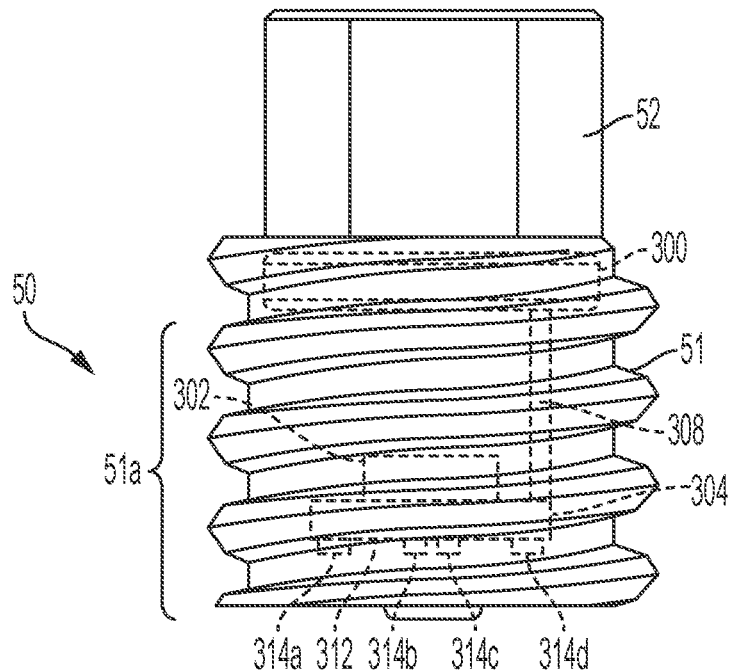
FIG. 15B illustrates a side view of a load sensing assembly mounted to a set screw according to an embodiment.
Figure 15D:
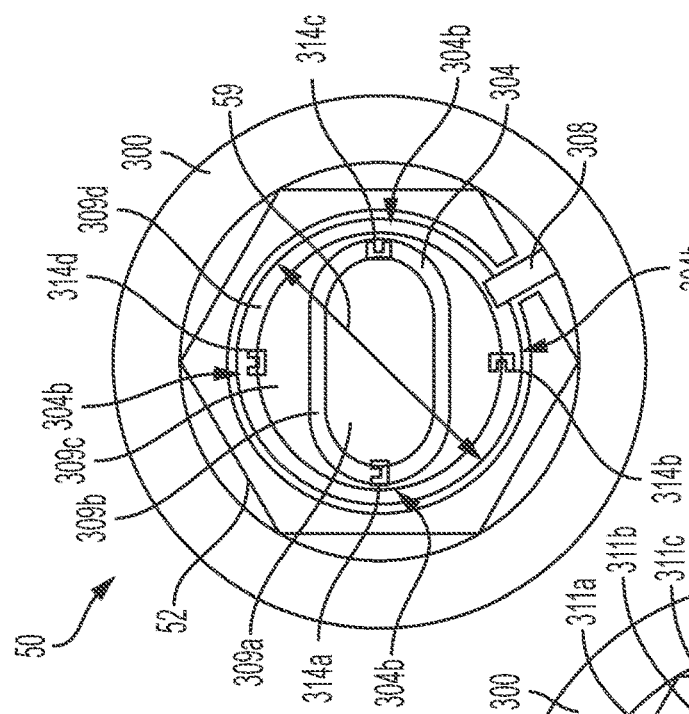
FIGS. 15C-15E illustrate bottom views taken at cross-section A-A in FIG. 15A of sensors positioned on the load sensing assembly according to an embodiment.
Figure 15E:
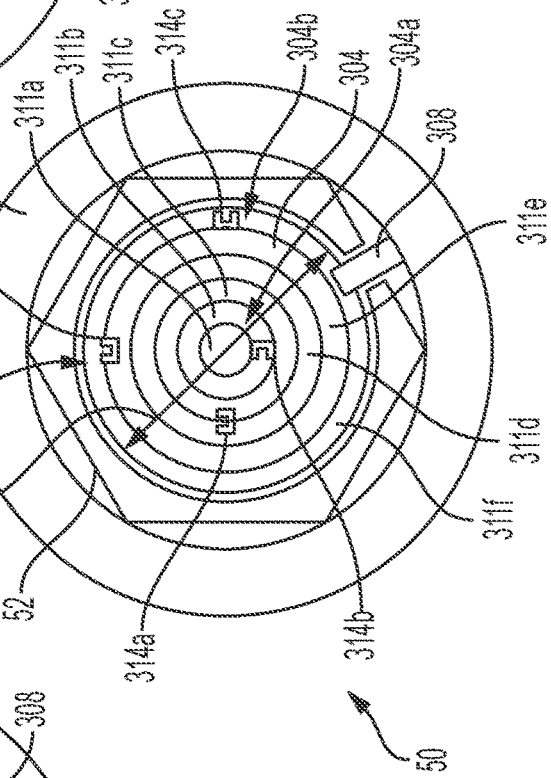
Figure 15C:
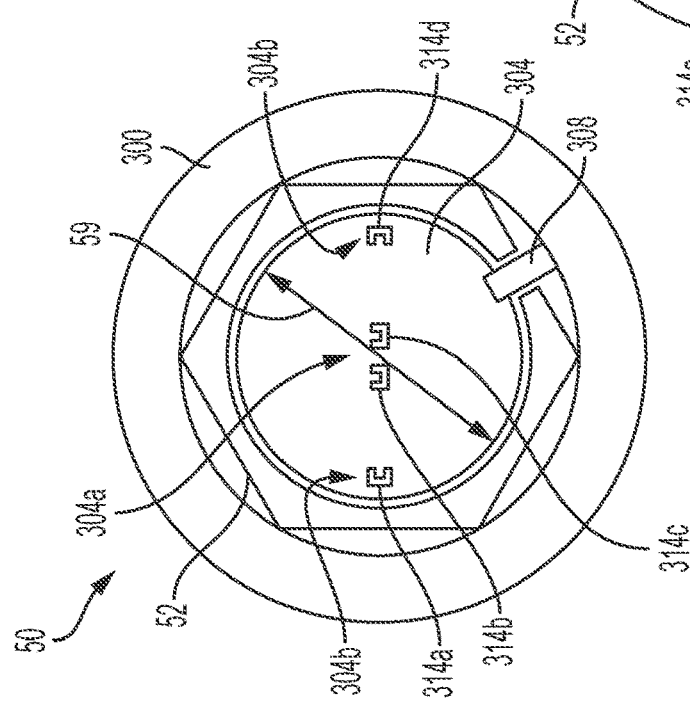

FIG. 15A illustrates a side view of a load sensing assembly mounted to the set screw 50 according to an embodiment. FIG. 15B illustrates a side view of a load sensing assembly mounted to the set screw 50 according to an embodiment. FIGS. 15C-15E illustrate bottom views taken at cross-section A-A in FIG. 15A of sensors positioned on the load sensing assembly according to an embodiment.

In one or more embodiments, the set screw 50, external threads 51, driving feature 52, antenna 300, integrated circuit 302, electronics component 304, and connecting member 308 include one or more of the same features discussed above with respect to the load sensing assembly mounted to the set screw 50 as described in FIGS. 3 through 5. Accordingly, a description of these same features is not repeated.

In one or more cases, the driving feature 52 of the set screw 50 may be positioned on top of the proximal end of the external threads 51. The driving feature 57 is configured to receive a tool, such as a screw driver, during engagement with the anchoring member 30. The driving feature 52 may include a bore 59 that extends from an outer top surface of the break-off head 58 and into a portion of the threaded portion 51*a* of the set screw 50. In one or more cases, the bore 59 may have a cylindrically shaped opening when view from a top surface of the set screw 50*a*. In one or more other cases, the bore 59 may have a star shaped opening, e.g., a shape to receive a hexalobe screw driver, with an inner cylindrically shaped opening when viewed from a top surface of the set screw 50*a*. The bore 59 may provide a working area for placing one or more sensors, such as sensors 314*a*, 314*b*, 314*c*, and 314*d* within the set screw 50. For the cases in which the bore 59 has a star shaped opening with an inner cylindrically shaped opening, the working area of the inner cylindrically shaped opening may be 2 to 5 mm in diameter, and more preferably at or about 3.65 mm in diameter. For the cases in which the bore 59 has a cylindrically shaped opening, the working area for the cylindrically shaped opening may be 3 to 7 mm in diameter, and more preferably at or about 5.35 mm in diameter. For the cases in which strain gauges are used as sensors 314*a*, 314*b*, 314*c*, and 314*d* in the driving feature 52 having the cylindrically shaped bore 59, the strain gauges may experience higher strain values than a driving feature 52 having the star shaped opening with an inner cylindrically shaped bore 59.

The driving feature 52 may have an external shape configured to engage with a tool, such as a screw driver, to rotate the set screw 50. The driving feature 52 may be configured in an external shape to enable a positive, non-slip engagement of the driving feature 52 by the tool. For example, in one or more cases, the outer perimeter of the driving feature 52 may be configured in a hexagonal shape. In one or more other cases for example, the outer perimeter, that is, the outer surface, of the driving feature 52 may be configured in a square shape, pentagonal shape, star shape, or the like. The driving feature 52 may include a slot, similar to slot 53, for receiving or routing electronic connections as illustrated in FIGS. 13A and 13B. In one or more cases, the driving feature 52 may be configured to break-off from the threaded portion 51*a*. In one or more other cases, the driving feature 52 may configured to not break-off from the threaded portion 51*a*.

In one or more cases, the antenna 300, connecting member 308, integrated circuit 302, and the electronics component 304 may be arranged in a similar manner and configured to operate in a similar manner as discussed with respect to FIGS. 3 and 4B. In one or more cases, the antenna 300 is configured to transmit signals from at least one of the integrated circuit 302, the electronics component 304, and sensors 314*a*, 314*b*, 314*c*, and 314*d* to a reader. In one or more cases, the antenna 300 is configured to receive signals from the reader. For example, the antenna 300 may receive an ON signal from reader, in which the ON signal powers on the load sensing assembly. In one or more cases, the antenna 300 may be sized to fit around a portion of the driving feature 52, as shown in FIG. 15A, and/or at least a portion of the exterior of the set screw 50, as shown in FIG. 4A. In one or more other cases, the antenna 300 may be sized to fit within a portion of the bore 59 of the threaded portion 51*a*, as shown in FIG. 15B, and/or within a portion of the central opening of the set screw 50, as shown in FIG. 4B. In one or more cases, the antenna 300 includes a ferrite core configured to amplify the transmission signals of the antenna 300.

In one or more cases, the sensors 314*a*, 314*b*, 314*c*, and 314*d* may be connected to a portion of the bore 59 of the set screw 50 in any suitable manner including, without limitation via an adhesive. The sensors 314*a*, 314*b*, 314*c*, and 314*d* may be strain gauges, impedance sensors, pressure sensors, capacitive sensors, temperature sensors, or the like. The sensors 314*a*, 314*b*, 314*c*, and 314*d* may be connected to a portion of the bore 59, i.e., the central opening. For the cases in which the sensors 314*a*, 314*b*, 314*c*, and 314*d* are strain gauges, the sensors 314*a*, 314*b*, 314*c*, and 314*d* may be positioned to measure a force between the set screw 50 and the longitudinal member 100 when the set screw 50 engages with the anchoring member 30, e.g., a nominal clamping force. The sensors 314*a*, 314*b*, 314*c*, and 314*d* may be operably connected to a bottom surface 312 of the electronics component 304. The sensors 314*a*, 314*b*, 314*c*, and 314*d* may directly interface with the set screw 50 and the electronics component 304. For the cases in which the sensors 314*a*, 314*b*, 314*c*, and 314*d* are temperature sensors, the sensors 314*a*, 314*b*, 314*c*, and 314*d* may be positioned above the integrated circuit 302. For the cases in which the sensors 314*a*, 314*b*, 314*c*, and 314*d* are capacitive sensors may be connected to a portion of the bore 59. In one or more cases, the set screw 50 may include all of the same type of sensors, for example, the set screw 50 may include all strain gauges. In one or more other cases, the set screw 50 may include a mix of sensors, for example, the set screw 50 may include strain gauges and temperature sensors.

FIGS. 15C-15E illustrate bottom views taken at cross-section A-A in FIG. 15A of sensors positioned on the load sensing assembly according to an embodiment. It should be noted that FIGS. 15C-15E illustrate embodiments that utilize four sensors, such as sensors 314*a*, 314*b*, 314*c*, and 314*d*; however, it should be understood that embodiments are contemplated that use more than 4 sensors and that use less than 4 sensors.

In one or more cases, the sensors 314*a*, 314*b*, 314*c*, and 314*d* may be linearly arranged across the electronics component 304, as shown in FIG. 15C. That is, the sensors 314*a*, 314*b*, 314*c*, and 314*d* may be linearly arranged across the bore 59, i.e., the central opening, of the set screw 50. The sensors 314*a*, 314*b*, 314*c*, and 314*d* may directly interface with the set screw 50 and the electronics component 304. In one or more cases in which the sensors are linearly arranged, two sensors, such as sensors 314*b* and 314*c*, may be arranged in close proximity to one another over a central portion 304*a* of the electronics component 304, and two other sensors, such as sensors 314*a* and 314*d*, may be each arranged on opposite sides from one another on an outer portion 304*b* of the electronics component 304. For example, the sensor 314*a* may be arranged on the outer portion 304*b*, e.g., a distal end, of the electronics component 304, and the sensor 314*d* may be arranged on the outer portion 304*b*, e.g., of the electronics component 304 opposite the sensor 314*a*. In one or more other cases in which the sensors are linearly arranged, the sensors may be linearly arranged on the electronics component 304, such that there is equal spacing between each of the sensors. In one or more cases, the two sensors 314*b* and 314*c* arranged in close proximity to one another may be active strain gauges configured to measure the greatest area of strain on the set screw 50. The two sensors 314a and 314d arranged on the outer portion 304b of the electronics component 304 may be compensating strain gauges configured to measure areas of lesser strain than those measured by sensors 314b and 314c.

The sensors 314a, 314b, 314c, and 314d are illustrated in FIG. 15C as being strain gauges having a "U" shape or substantially U-like shape. In one or more cases, the opening of the U-shaped sensor 314a and the opening of the U-shaped sensor 314d may face each other. In one or more cases, the opening of the U-shaped sensor 314b and the opening of the U-shaped sensor 314c may face away from one another. In one or more cases, the openings of the U-shaped sensors 314a and 314d may be positioned to face towards the central portion 304a of the electronics component 304 and the bore 59. In one or more cases, the openings of the U-shaped sensors 314b and 314c may be positioned to face towards the outer portion 304b of the electronics component 304 and the bore 59.

In one or more cases, the sensors 314a, 314b, 314c, and 314d may be circumferentially arranged around the electronics component 304. The sensors 314a, 314b, 314c, and 314d may be circumferentially arranged around the outer portion 304b of the electronics component 304, as shown in FIG. 15D. That is, the sensors 314a, 314b, 314c, and 314d may be circumferentially arranged around the outer portion of the bore 59, i.e., the central opening, of the set screw 50. The sensors 314a, 314b, 314c, and 314d may directly interface with the set screw 50 and the electronics component 304. In one or more cases, the two sensors 314a and 314c may be active strain gauges arranged around the outer portion 304b of the electronics component 304 in the areas of greatest strain on the set screw 50. The two sensors 314b and 314d may be compensating strain gauges arranged on the outer portion 304b of the electronics component 304 in the areas of lesser strain than those measured by sensors 314a and 314c. For example, for the cases in which the bore 59 has a star shaped opening with an inner cylindrically shaped opening, the sensors 314a and 314c may be positioned to measure areas 309a and 309b, in which the strain of area 309a ranges from about 0.0054995 to about 0.0035 and the strain of area 309b ranges from about 0.0035 to about 0.003. The sensors 314b and 314d may be positioned to measure areas 309c and 309d, in which the strain of area 309c ranges from about 0.003 to about 0.0025 and the strain of area 309d ranges from about 0.0025 to about 0.002.

The sensors 314a, 314b, 314c, and 314d are illustrated in FIG. 15D as being strain gauges having a "U" shape or substantially "U"-like shape. In one or more cases, the openings of the U-shaped sensors 314c and 314d may be positioned to face away from the central portion 304a of the electronics component 304 and the bore 59 and towards the outer portion 304b. In one or more cases, the opening of the U-shaped sensor 314b may be positioned to face, following an arc-like path from the sensor 314b to the sensor 314a, a rear surface of the U-shaped sensor 314a. In one or more cases, the opening of the U-shaped sensor 314a may be positioned to face, following an arc-like path from the sensor 314a to the sensor 314d, a side surface of the U-shaped sensor 314a. The openings of the U-shaped sensors 314a and 314d may be positioned to face in the same direction. The openings of the U-shaped sensors 314b and 314c may be positioned to face in the same direction. The openings of the U-shaped sensors 314a, 314b, 314c, and 314d may be positioned to face towards the outer portion 304b of the electronics component 304 and the bore 59.

In one or more cases, a portion of the sensors may be arranged on the central portion 304a of the electronics component 304, and another portion of the sensors may be arranged on the outer portion 304b of the electronics component 304. For example, sensors 314a and 314b may be arranged on the central portion 304a of the electronics component 304, and sensors 314d and 314c may be arranged on the outer portion 304b of the electronics component 304, as shown in FIG. 15E. In one or more cases, the two sensors 314a and 314b arranged on the central portion 304a of the electronics component 304 may be active strain gauges configured to measure the greatest area of strain on the set screw 50. The two sensors 314d and 314c arranged on the outer portion 304b of the electronics component 304 may be compensating strain gauges configured to measure areas of lesser strain than those measured by sensors 314a and 314b. For example, for the cases in which the bore 59 has a cylindrically shaped opening, the sensor 314b may be positioned to measure areas 311a, 311b, and 311c, in which the strain of area 311a ranges from about 0.009 to about 0.008, the strain of area 311b ranges from about 0.008 to about 0.007, and the strain of area 311c ranges from about 0.007 to about 0.006. The sensor 314a may be positioned to measure areas 311c and 311d, in which the strain of area 311b ranges from about 0.006 to about 0.005. The sensor 314d may be positioned to measure areas 311e and 311f, in which the strain of area 311e ranges from about 0.005 to about 0.004 and the strain of area 311f ranges from about 0.004 to about 0.003. The sensor 314c may be positioned to measure area 311f.

In one or more cases, using the center of the electronics component 304 as a reference point, the sensors 314c and 314d may be positioned at or about 90° from one another. In one or more cases, using the center of the electronics component 304 as a reference point, the sensors 314a and 314b may be positioned at or about 90° from one another. The sensors 314a, 314b, 314c, and 314d are illustrated in FIG. 15E as being strain gauges having a "U" shape or substantially "U"-like shape. In one or more cases, the openings of the U-shaped sensors 314c and 314d may be positioned to face away from the central portion 304a of the electronics component 304 and the bore 59 and towards the outer portion 304b. In one or more cases, the opening of the U-shaped sensor 314b may be positioned to face, following an arc-like path from the sensor 314b to the sensor 314a, a rear surface of the U-shaped sensor 314a. In one or more cases, the opening of the U-shaped sensor 314a may be positioned to face, following an arc-like path from the sensor 314a to the sensor 314d, a side surface of the U-shaped sensor 314a. The openings of the U-shaped sensors 314a and 314d may be positioned to face in the same direction. The openings of the U-shaped sensors 314b and 314c may be positioned to face in the same direction. The openings of the U-shaped sensors 314a, 314b, 314c, and 314d may be positioned to face towards the outer portion 304b of the electronics component 304 and the bore 59.

As used herein, the term "about" in reference to a numerical value means plus or minus 10% of the numerical value of the number with which it is being used.

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A load sensing assembly for a spinal implant, the load sensing assembly comprising:
 a set screw comprising a central opening that extends from a first end of the set screw toward a second end of the set screw, wherein the second end of the set screw is configured to engage with an anchoring member receiving a rod;
 an antenna;
 an integrated circuit in communication with the antenna, wherein the integrated circuit is positioned within the central opening of the set screw; and
 a plurality of sensors in connection with the integrated circuit, wherein the plurality of sensors are located within the central opening of the set screw in proximity to the second end of the set screw,
 wherein at least one sensor of the plurality of sensors comprises a strain gauge configured to measure a localized force between the second end of the set screw and the rod.

2. The load sensing assembly of claim 1, wherein the antenna comprises an opening therethrough, wherein the antenna circumferentially surrounds at least a portion of the set screw.

3. The load sensing assembly of claim 1, wherein at least a portion of the antenna is positioned in the central opening of the set screw.

4. The load sensing assembly of claim 1, further comprising an electronics component, wherein the electronics component comprises a top surface, a bottom surface, and one or more electrical circuits.

5. The load sensing assembly of claim 4, wherein the plurality of sensors further comprise at least one of: impedance sensors, pressure sensors, and capacitive sensors.

6. The load sensing assembly of claim 4, wherein the plurality of sensors are operably connected to the bottom surface of the electronics component.

7. The load sensing assembly of claim 1, wherein the plurality of sensors are linearly arranged across the central opening of the set screw.

8. The load sensing assembly of claim 1, wherein the plurality of sensors are circumferentially arranged around an outer portion of the central opening of the set screw.

9. The load sensing assembly of claim 1, wherein a first portion of the plurality of sensors are arranged around a central portion of the central opening of the set screw, and a second portion of the plurality of sensors are arranged around an outer portion of the central opening of the set screw.

10. The load sensing assembly of claim 9, wherein the first portion of the plurality of sensors are circumferentially arranged around the central portion, and the second portion of the plurality of sensors are circumferentially arranged around the outer portion.

11. A load sensing assembly for a spinal implant, the load sensing assembly comprising:
 a set screw extending from a first end to a second end, wherein the second end of the set screw is configured to engage with an anchoring member receiving a rod;
 an antenna;
 an electronics component comprising one or more electrical circuits, wherein the electronics component is operably connected to the antenna;
 an integrated circuit operably connected to at least a portion of the electronics component; and
 a plurality of sensors in communication with the integrated circuit, wherein at least one of the plurality of sensors are configured to measure a localized force between the second end of the set screw and the rod,
 wherein the plurality of sensors are arranged on and operably connected to the bottom surface of the electronics component.

12. The load sensing assembly of claim 11, wherein:
 the antenna comprises a radio frequency identification coil,
 the antenna is configured to circumferentially surround an opening of the set screw adjacent the first end.

13. The load sensing assembly of claim 11, wherein at least a portion of the antenna is positioned in a central opening of the set screw.

14. The load sensing assembly of claim 11, wherein the plurality of sensors comprise at least one of strain gauges, impedance sensors, pressure sensors, and capacitive sensors.

15. The load sensing assembly of claim 11, wherein the plurality of sensors are linearly arranged across a central opening of the set screw.

16. The load sensing assembly of claim 11, wherein the plurality of sensors are circumferentially arranged around an outer portion of a circular shaped opening of the set screw.

17. The load sensing assembly of claim 11, wherein a portion of the plurality of sensors are circumferentially arranged around a central portion of a central opening of the set screw, and another portion of the plurality of sensors are circumferentially arranged around an outer portion of the central opening of the set screw.

18. The load sensing assembly of claim 11, wherein a first portion of the plurality of sensors are arranged around a central portion of a central opening of a set screw, and a second portion of the plurality of sensors are arranged around an outer portion of the central opening of the set screw.

19. The load sensing assembly of claim 18, wherein the first portion of the plurality of sensors are circumferentially arranged around the central portion, and the second portion of the plurality of sensors are circumferentially arranged around the outer portion.

* * * * *